(12) United States Patent
Du

(10) Patent No.: US 12,144,643 B2
(45) Date of Patent: Nov. 19, 2024

(54) WIRELESS SENSOR, MANUFACTURING METHOD THEREOF AND WOUND FLATNESS DETECTION SYSTEM

(71) Applicant: The First Affiliated Hospital of Xi'an Jiaotong University, Shaanxi (CN)

(72) Inventor: Huicong Du, Shaanxi (CN)

( * ) Notice: Subject to any disclaimer, the term of this patent is extended or adjusted under 35 U.S.C. 154(b) by 0 days.

(21) Appl. No.: 18/749,762

(22) Filed: Jun. 21, 2024

(65) Prior Publication Data

US 2024/0335161 A1 Oct. 10, 2024

(51) Int. Cl.
*A61B 5/00* (2006.01)
(52) U.S. Cl.
CPC .............. *A61B 5/445* (2013.01); *A61B 5/742* (2013.01); *A61B 2560/0204* (2013.01); *A61B 2560/045* (2013.01); *A61B 2562/043* (2013.01); *A61B 2562/125* (2013.01); *A61B 2562/164* (2013.01); *A61B 2562/166* (2013.01)
(58) Field of Classification Search
CPC . A61B 5/445; A61B 5/742; A61B 2560/0204; A61B 2560/045; A61B 2562/043; A61B 2562/125; A61B 2562/164; A61B 2562/166
See application file for complete search history.

(56) References Cited

FOREIGN PATENT DOCUMENTS

| CN | 108007480 A | 5/2018 |
|---|---|---|
| CN | 216386065 U | 4/2022 |

OTHER PUBLICATIONS

CN202311074015.8 Office Action dated Feb. 21, 2024, original Chinese, pp. 1-5.
CN202311074015.8 Office Action dated Feb. 21, 2024, English translation accessed Jun. 19, 2024, pp. 1-6.
CN202311074015.8 Notice of Allowance dated Apr. 24, 2024, original Chinese, 1 page.
CN202311074015.8 Notice of Allowance dated Apr. 24, 2024, English translation accessed Jun. 19, 2024 p. 1-2.

*Primary Examiner* — Scott M. Getzow
(74) *Attorney, Agent, or Firm* — Addison D. Ault; Richard P. Moerschell; IPGentleman Intellectual Property Services, LLC

(57) ABSTRACT

The present disclosure provides a wireless sensor, a manufacturing method thereof and a wound flatness detection system. The wireless sensor includes a sensing element, two elastomer-made encapsulation layers and a breathable fiber-made encapsulation layer; wherein the sensing element is manufactured by the following steps: step 1: preparing a thin film using a carbon-based polymer solution; step 2: using a low-energy laser to induce molecular reconstruction of carbon-based groups on surfaces of the thin film to form a resistance-sensitive layer; step 3: using a high-energy laser to modify, carbonize and cut the resistance-sensitive layer to form a patterned sensing element. The present disclosure solves the problems that existing pressure or tension sensors are extremely susceptible to static interference from the external environment and the human body, and the mechanical mismatch between the sensing layer and the substrate, as well as the impermeability problem.

8 Claims, 7 Drawing Sheets

WIRELESS SENSOR, MANUFACTURING METHOD THEREOF AND WOUND FLATNESS DETECTION SYSTEM

CROSS-REFERENCE TO RELATED APPLICATION

This application claims priority to Chinese Patent Application No. 202311074015.8, filed on Aug. 24, 2023 before the China National Intellectual Property Administration, the disclosure of which is incorporated herein by reference in entirety.

TECHNICAL FIELD

The present disclosure relates to the field of flexible sensors, and in particular to a wireless sensor, a manufacturing method thereof and a wound flatness detection system.

BACKGROUND

The speed of wound healing is not only related to factors such as the size of the wound, or the lifestyle, but also has a great relationship with the flatness/smoothness of the wound. Through investigation, it was found that flat/smooth wounds can provide the following benefits: First, a flat/smooth wound can promote the normal progress of healing; if the wound surface is smooth and even, the tissues around the wound can better contact to each other and grow, this helps promote cell regeneration and tissue repair, thus speeding up the healing and reducing the risk of infection. Second, a smooth wound helps reduce scar formation, if the wound surface is uneven, the tissue growth and connective tissue formation may be disrupted, leading to scarring. In contrast, a flat wound can better restore the integrity of the skin and reduce scarring, thereby improving the patient's appearance satisfaction and psychological satisfaction. Third, a smooth wound can also reduce discomfort and pain; if the wound edges are flat, there is less pull and pressure on the surrounding skin, reducing stinging and discomfort feeling, which is very important for patient comfort and smooth recovery process. Therefore, detecting/testing the flatness/smoothness of postoperative wounds can ensure the smooth progress of wound healing and reduce the occurrence of adverse consequences.

Currently, flexible sensors are mainly used to detect postoperative wound flatness. Existing flexible sensors generally implement sensing functions based on pressure or tension and cannot meet the needs of good wound flatness detection. This is mainly due to the fact that existing pressure or tension sensors generally adopt capacitive sensors in order to obtain higher sensitivity, however, capacitive sensors are extremely susceptible to interference from the external environment and human body static electricity, and therefore are not suitable as detection equipment that directly contacts human skin. Moreover, existing tension sensors are generally implemented through wrinkles and cracks in conductors, which to a certain extent causes a problem of mechanical mismatch between the sensing layer and the substrate. In addition, since wounds generally have high requirements for air permeability, it is difficult for traditional flexible sensors to meet the air permeability requirements. Therefore, there is a need to provide a wireless sensor that can meet the breathability requirements and be used to detect the flatness of postoperative wounds.

SUMMARY

In order to solve the problems that existing pressure or tension sensors are extremely susceptible to static interference from the external environment and the human body, the mechanical mismatch between the sensing layer and the substrate, as well as the impermeability problem, the purpose of the present disclosure is to provide a wireless sensor for detecting postoperative wound flatness, which can meet the air permeability requirements, a manufacturing method of the wireless sensor and a wound flatness detection system.

In the embodiments of the present disclosure, molecular reconstruction can occur on the surface of a flexible substrate under the induction of a low-energy laser to form a resistance-sensitive layer, then it is modified, carbonized and cut again by a high-energy laser to form a sensing element, and then the sensing element is encapsulated by using elastomer-made encapsulation layers and a breathable fiber-made encapsulation layer to form a wireless sensor.

The processing method of the present disclosure combines high multi-layer matching degree and the ability to resist environmental interference. Moreover, since wounds generally have high requirements for breathability, the present disclosure uses direct encapsulation of breathable fibers to improve patient comfort and recovery effects, and achieve a design with controllable breathability and viscosity.

In order to achieve the above objects, the technical solutions of the present disclosure are as follows.

A wireless sensor, comprising a sensing element, two elastomer-made encapsulation layers and a breathable fiber-made encapsulation layer, wherein the sensing element is arranged between the two elastomer-made encapsulation layers, and the breathable fiber-made encapsulation layer is disposed on one of the elastomer-made encapsulation layers;

wherein the sensing element is manufactured by the following steps:

step 1: preparing a thin film using a carbon-based polymer solution;

step 2: using a low-energy laser to induce molecular reconstruction of carbon-based groups on surfaces of the thin film to form a resistance-sensitive layer;

step 3: using a high-energy laser to modify, carbonize and cut the resistance-sensitive layer to form a patterned sensing element.

The patterning process of the sensing element in the present disclosure includes two steps: the first step is to use a low-energy laser to induce surface molecular reconstruction to form a sensing layer that can detect the flatness of the wound; the second step is to use a high-energy laser to modify and cut the edges. In this way, it helps convert the wound flatness into a resistance signal and improves detection sensitivity. Moreover, the multiple electrode pins on the sensing element have different degrees of stretching on the uneven surface, which can achieve different resistance distribution states. As a result, the partial voltages after the common potential port are different, resulting in differences in potential distribution at different test points, to determine the flatness of the wound.

Further, in step 1, the preparing a thin film using a carbon-based polymer solution comprises:

evenly coating the carbon-based polymer solution on a surface of a substrate, drying the surface of the substrate to remove solvent, and then performing an annealing treatment to the substrate to obtain the thin film.

Further, the carbon-based polymer solution is a polyamic acid solution; the substrate is a polyimide substrate or a glass substrate.

Further, the annealing treatment is performed in such a condition that an annealing temperature is 150-250° C. and an annealing time is 5-60 minutes.

Further, the drying temperature is 90 to 100° C.

Further, in step 2, the low-energy laser has a power of 6-20 W.

Further, in step 3, the high-energy laser has a power of 20-35 W.

In the present disclosure, the condition for using a laser to induce surface molecular reconstruction is that the input energy of the laser needs to meet the minimum energy requirement for the reconstruction of molecular bonds without completely cutting/removing the substrate. Generally, a laser power of 6-20 W is selected. The laser input energy for edge modification, carbonization and cutting is generally very high, generally 20-30 W or even more than 30 W.

Further, the sensing element has a plurality of electrode pins at one side.

Further, the elastomer-made encapsulation layers comprise SEBS layers, and the SEBS layers are formed by coating and solidifying a SEBS solution on surfaces of the sensing element;

the breathable fiber-made encapsulation layer comprises an adhesive layer and a fiber film, and the fiber film is connected to the elastomer-made encapsulation layer through the adhesive layer.

Further, the sensing element, the elastomer-made encapsulation layer and the breathable fiber-made encapsulation layer have the same shape; the sensing element, the elastomer-made encapsulation layer and the breathable fiber-made encapsulation layer have the same dimension.

The present disclosure also provides a method for manufacturing a wireless sensor, comprising the following steps:

S1: preparing a thin film using a carbon-based polymer solution;

S2: using a low-energy laser to induce molecular reconstruction of carbon-based groups on surfaces of the thin film to form a resistance-sensitive layer;

S3: using a high-energy laser to modify, carbonize and cut the resistance-sensitive layer to form a patterned sensing element;

S4: coating and solidifying a SEBS solution on one surface of the sensing element to form a SEBS layer; after peeling and flipping, coating and solidifying a SEBS solution on the other surface of the sensing element to form another SEBS layer; using a high-energy laser to carbonize and cut two SEBS layers to form patterned elastomer-made encapsulation layers;

S5: encapsulating a fiber film on one of the elastomer-made encapsulation layers through adhesive; using a high-energy laser to carbonize and cut the fiber film to form a patterned breathable fiber-made encapsulation layer.

Further, in step S1, the preparing a thin film using a carbon-based polymer solution comprises: evenly coating the carbon-based polymer solution on a surface of a substrate, drying the surface of the substrate to remove solvent, and then performing an annealing treatment to the substrate to obtain the thin film.

Further, the carbon-based polymer solution is a polyamic acid solution; the substrate is a polyimide substrate or a glass substrate.

Further, the annealing treatment is performed in such a condition that an annealing temperature is 150-250° C. and an annealing time is 5-60 minutes.

The present disclosure also provides a wound flatness detection system, comprising a microprocessor, an operational amplifier, a digital-analog converter, a wireless transmitter, a display and the wireless sensor according to claim 1;

the wireless sensor is configured to sense a flatness of a wound surface and convert it into a resistance signal;

the operational amplifier is configured to receive the resistance signal and convert it into a voltage signal;

the digital-analog converter is configured to receive the voltage signal and convert it into a digital signal;

the wireless transmitter is configured to receive the digital signal and wirelessly transmit it to the microprocessor;

the microprocessor is configured to receive the digital signal and send it to the display.

The wireless sensor of the present disclosure uses universal flexible and breathable ultra-thin materials to realize the detection and recovery observation of postoperative wounds, and has important application value. The combination of multi-layer elastomer composite and breathable fiber layer achieves viscosity control and convenient replacement. Mass production and large-scale manufacture can be achieved through laser processing. The present disclosure also proposes an effective method for converting wound flatness into digital electrical signals, converting contour signals into variable electrical signals through integrated circuits and then wirelessly transmitting them to the user interface, which provides a solid foundation for practical applications.

Further, it also includes a power supply, which is electrically connected to the microprocessor, the operational amplifier, the digital-analog converter, the wireless transmitter, the display, and the wireless sensor.

Beneficial Effects of the Present Disclosure

I. The present disclosure uses a carbon-based polymer solution to prepare a thin film, and then uses laser as an energy source to achieve patterning of the sensing element through two-step laser induction. In this way, it is beneficial to converting the flatness of the wound into a resistance signal and improving detection sensitivity.

II. The sensing element of the present disclosure is encapsulated in the upper and lower layers and composited with a fiber layer, so that the wireless sensor has both high multi-layer matching degree and the ability to resist environmental interference, and it can avoid static interference from the human body, and make the sensing layer and the substrate meet mechanical matching requirement, and it can achieve a breathable and viscosity-controllable design.

III. The wireless sensor of the present disclosure can convert the postoperative wound flatness into changing resistance signals, and the signals are read and transmitted through a wireless small circuit to monitor the wound suturing and healing conditions in real time on the user interface, to realize the detection and recovery observation of postoperative wounds. It has important application value.

Figure 1:
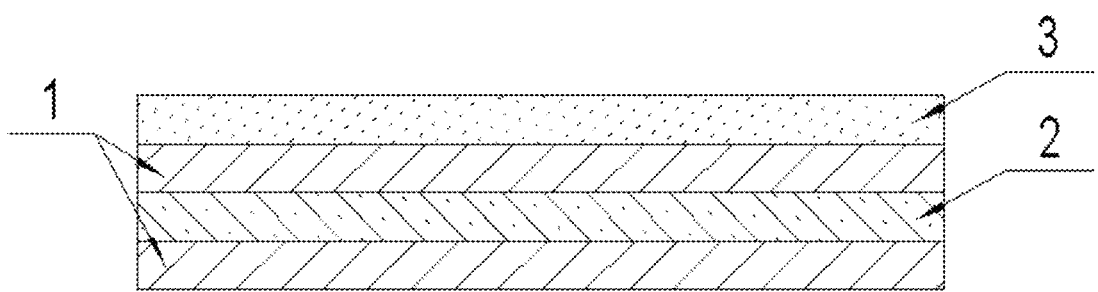
FIG. 1 is a schematic structural view of a wireless sensor in one embodiment.

In the drawings: 1. Elastomer-made encapsulation layer; 2. Sensing element; 21. Electrode pin; 3. Breathable fiber-made encapsulation layer.

DETAILED DESCRIPTION OF EMBODIMENTS

In order to make the purposes, technical solutions and advantages of the present disclosure clearer, the present disclosure will be further described in detail below in conjunction with examples. It should be understood that the specific examples/embodiments described here are only used to explain the present disclosure but are not intended to limit the present disclosure.

All embodiments obtained by those of ordinary skill in the art based on the embodiments of the present disclosure without creative efforts fall within the scope of protection of the present disclosure.

Since detecting the flatness of postoperative wounds can ensure the smooth progress of the wound healing and reduce the occurrence of adverse consequences, a flexible sensor is usually installed on the surface of the wound to detect the flatness of postoperative wound. However, the currently used flexible sensors, for example, pressure sensors and tension sensors, all use capacitive sensing in order to obtain higher sensitivity. The capacitive sensors are extremely susceptible to static interference from the external environment and the human body, and are not suitable as a skin testing equipment for direct contact with the human body. Moreover, existing tension sensors are generally implemented through wrinkles and cracks in conductors, which to a certain extent causes a problem of mechanical mismatch between the sensing layer and the substrate. In addition, since wounds generally have high requirements for air permeability, it is difficult for traditional flexible sensors to meet the air permeability requirements.

Therefore, in view of the problems that existing flexible sensors are extremely susceptible to static interference from the external environment and the human body, and the mechanical mismatch between the sensing layer and the substrate, as well as the difficulty in meeting the breathability requirements, the following embodiments of the present disclosure provide a wireless sensor for detecting postoperative wound flatness, which can meet the air permeability requirements, a corresponding manufacturing method of the wireless sensor and a wound flatness detection system.

The following are specific examples of the wireless sensor, its manufacturing method, and the wound flatness detection system.

Example 1

Figure 2:
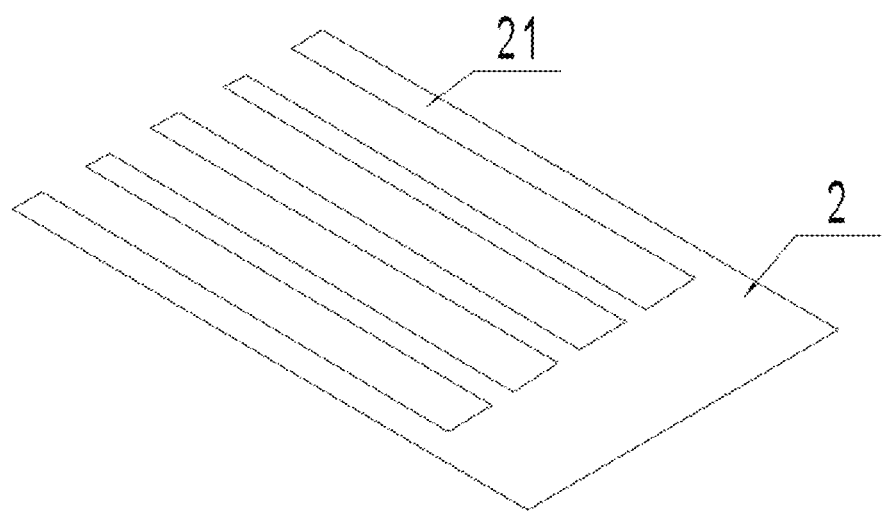
FIG. 2 is a schematic structural view of a sensing element in this embodiment.
Figure 3:
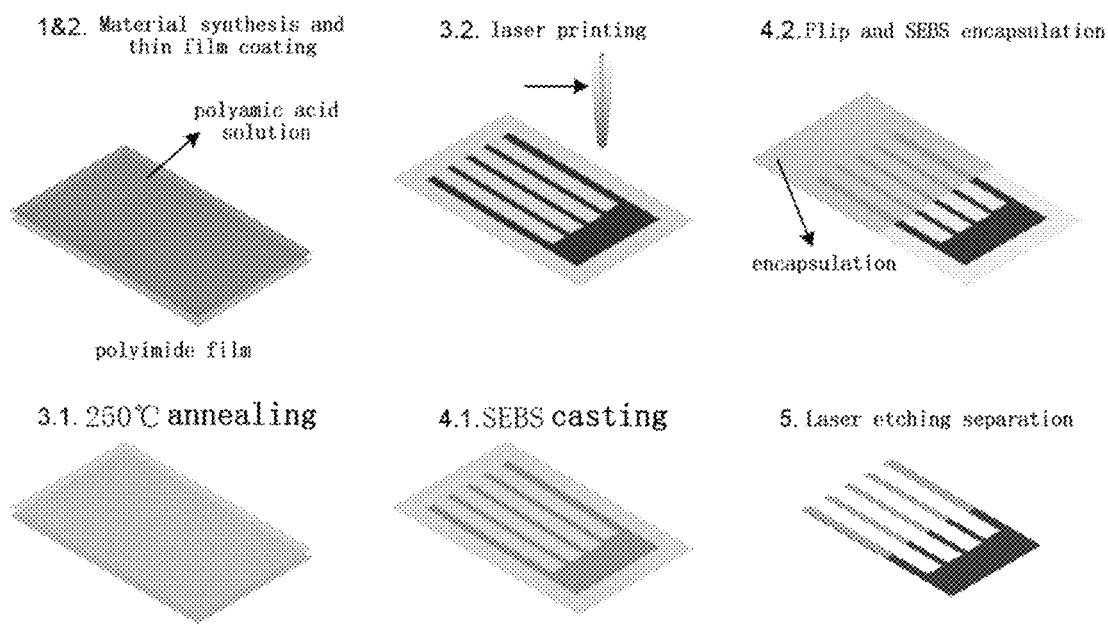
FIG. 3 is a design flow chart of the wireless sensor in this embodiment.

Please refer to FIGS. 1 to 3, there is provided a wireless sensor according to an embodiment of the present disclosure, including a sensing element 2, elastomer-made encapsulation layers 1 and a breathable fiber-made encapsulation layer 3; the sensing element 2 is disposed between two elastomer-made encapsulation layers 1, the breathable fiber-made encapsulation layer 3 is arranged on one of the elastomer-made encapsulation layers 1; one side of the sensing element 2 has a plurality of electrode pins 21. Specifically, the shapes of the sensing element 2, the elastomer-made encapsulation layers 1 and the breathable fiber-made encapsulation layer 3 are all consistent; the sizes of the sensing element 2, the elastomer-made encapsulation layers 1 and the breathable fiber-made encapsulation layer 3 are all the same.

Herein, the multiple electrode pins 21 of the sensing element 2 can convert the postoperative wound flatness into changing resistance signals, and then the signals are read and transmitted through a wireless small circuit, so as to monitor the wound suturing and healing conditions on the user interface, to realize a real-time monitoring. That is to say, the multiple electrode pins on the sensing element have different degrees of stretching on the uneven surface, which can achieve different resistance distribution states, resulting in different partial voltages after the common potential port, resulting in differences in potential distribution at different test points. The difference can be used to determine the flatness of the wound, which solves the problem that existing flexible sensors are susceptible to static interference from the external environment and the human body due to the use of capacitive sensing.

Disposing the sensing element 2 between two elastomer-made encapsulation layers 1 enables the wireless sensor to have both high multi-layer matching degree and the ability to resist environmental interference, and it can avoid static interference from the human body and make mechanical matching between the sensing layer and the substrate, which solves the problem of mechanical mismatch between the sensing layer and the substrate that exists in existing flexible sensors due to sensing through wrinkles and cracks in the conductor.

Using the elastomer-made encapsulation layers 1 and the breathable fiber-made encapsulation layer 3 to encapsulate the sensing element 2 can enable the wireless sensor to meet the breathability requirements of the wound, improve patient comfort and recovery effects, and achieve a design with controllable breathability and viscosity. This solves the problem that existing flexible sensors are difficult to meet air permeability requirements.

Figure 4:
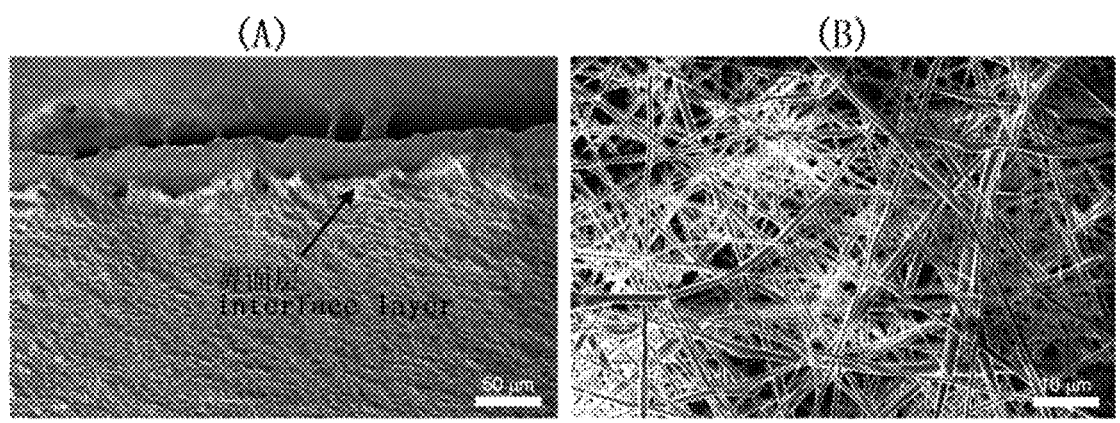
FIG. 4 shows scanning electron microscope photos of an adhesive layer (A) and a breathable fiber-made encapsulation layer (B) of the wireless sensor.

The elastomer-made encapsulation layer 1 includes a SEBS layer, which is formed by coating the SEBS solution on the surface of the sensing element 2 and solidifying it; the breathable fiber-made encapsulation layer 3 includes an adhesive layer and a fiber film, and the fiber film is connected to one of the elastomer-made encapsulation layers 1 through the adhesive layer. An adhesive layer is bonded to another elastomer-made encapsulation layer 1. FIG. 4 shows scanning electron microscope photos of the adhesive/viscous layer (A) and the breathable fiber-made encapsulation layer (B) of the wireless sensor, it is used to adjust the viscosity of the composite sensor layers and facilitate handheld replacement. From FIG. 4(B), the fiber layer is clearly shown and it has certain pores to meet the air permeability requirements.

When preparing the wireless sensor, it also includes an electrode arranged on one side of the sensing element 2, and a protective layer arranged on the electrode; the protective layer is the adhesive layer. The protective layer and the sensing element 2 are both arranged between the two elastomer-made encapsulation layers 1.

In this embodiment, the sensing element 2 is prepared by the following method:

Step 1: The carbon-based polymer solution is evenly coated on the surface of the substrate, dried to remove the solvent, and then annealed to obtain a thin film. The carbon-based polymer solution is a polyamic acid solution; the substrate is a polyimide substrate or a glass substrate; the conditions for the annealing treatment are: the annealing temperature is 150 to 250° C. and the annealing time is 5 to 60 minutes.

Step 2: A low-energy laser is used to induce molecular reconstruction of carbon-based groups on the surface of the thin film to form a resistance-sensitive layer; the power of the low-energy laser is 6 to 20 W.

Step 3: A high-energy laser is used to modify, carbonize and cut the resistance-sensitive layer to form a patterned sensing element. The power of high-energy laser is 20~35 W.

In the embodiment of the present disclosure, the patterning process of the sensing element 2 includes two steps: the first step is to use a low-energy laser to induce surface molecular reconstruction to form a sensing layer that can detect the flatness of the wound; the second step is to use a high-energy laser to modify and cut the edges. This helps convert the wound flatness into a resistance signal and improves detection sensitivity.

Moreover, the multiple electrode pins on the sensing element have different degrees of stretching on the uneven surface, which can achieve different resistance distribution states. As a result, the partial voltages after the common potential port are different, resulting in differences in potential distribution at different test points. In this way, it determines the flatness of the wound.

Herein, the condition for using laser to induce surface molecular reconstruction is that the input energy of the laser needs to meet the minimum energy requirement for the reconstruction of molecular bonds without completely removing the substrate. Generally, a laser power of 6-20 W is selected. The laser input energy for edge modification, carbonization and cutting is generally very high, generally 20-30 W or even more than 30 W, preferably 20-35 W. In this embodiment, the laser input energy used for modification, carbonization and cutting from the high-energy laser is not limited to 20-35 W.

Below we provide a detailed description of the preparation of the above wireless sensor.

Example 2

A method for manufacturing a wireless sensor, including the following steps:

S1. Form a Sensing Element

Select a glass substrate, cut it to twice the size of the sensor, and use oxygen plasma to clean the surface of the glass substrate for two minutes. Coat a polyamic acid solution evenly on the surface of the glass substrate. Due to the high viscosity of the polyamic acid solution, it needs to be left in the air for an hour to form a smooth surface. Place the sample on the heating stage, bake at 100° C. for one hour to remove the solvent, and then anneal at 150° C. for five minutes and 250° C. for one hour to obtain a thin film.

A $CO_2$ laser is used to induce molecular reconstruction of carbon-based groups on the surface of the film using a low-energy laser with a power of 6 to 20 W to form a resistance-sensitive layer.

A high-energy laser with a power of 20 to 35 W is used to modify, carbonize and cut the resistive sensitive layer to form a patterned sensing element.

The sensing element is patterned at a grating speed of 25%-75%, and linewidth resolution can be further improved through high-resolution lenses.

S2. Encapsulating to Prepare the Sensor

S2.1. Drop the SEBS solution of linear triembedded (triblock) copolymer on the sensor surface to obtain a precursor sample. Place the precursor sample in a desiccator and vacuum it for five minutes to remove air bubbles. After leaving it overnight, the toluene solvent will evaporate. At this time, the sample is peeled off and attached to the surface of the glass substrate with its back side upward. The wire connection is covered with tape, and the SEBS solution is spin-coated again to form a stretchable elastomer-made encapsulation layer. Then use a high-power (greater than 30 W) laser to cut the sample to form a specific shape.

S2.2. Place the flexible double-sided ultra-thin tape with higher viscosity (such as Silbione) on the surface of the glass substrate, place the cut sensor on the surface of the tape, and encapsulate it with a fiber film with lower viscosity to form a breathable fiber-made encapsulation layer, and then use a high-power (greater than 30 W) laser to cut the sample, to obtain a wireless sensor.

Example 3

A method for manufacturing a wireless sensor, including the following steps:

S1. Form a Sensing Element

Select a PI tape as the substrate, cut it to twice the size of the sensor, and use oxygen plasma to clean the surface of the PI substrate for two minutes. Coat a polyamic acid solution evenly on the surface of the PI substrate. Due to the high viscosity of the polyamic acid solution, it needs to be left in the air for an hour to form a smooth surface. Place the sample on the heating stage, bake at 100° C. for one hour to remove the solvent, and then anneal at 150° C. for five minutes and 250° C. for one hour to obtain a thin film;

A $CO_2$ laser is used to induce molecular reconstruction of carbon-based groups on the surface of the film using a low-energy laser with a power of 6 to 20 W to form a resistance-sensitive layer.

A high-energy laser with a power of 20 to 35 W is used to modify, carbonize and cut the resistive sensitive layer to form a patterned sensing element.

The sensing element is patterned at a grating speed of 25%-75%, and linewidth resolution can be further improved through high-resolution lenses.

S2. Encapsulating to Prepare the Sensor

S2.1. Drop the SEBS solution of linear triembedded (triblock) copolymer on the sensor surface to obtain a precursor sample. Place the precursor sample in a desiccator and vacuum it for five minutes to remove air bubbles. After leaving it overnight, the toluene solvent will evaporate. At this time, the sample is peeled off and attached to the surface of the PI substrate with its back side upward. The wire connection is covered with tape, and the SEBS solution is spin-coated again to form a stretchable elastomer-made encapsulation layer. Then use a high-power (greater than 30 W) laser to cut the sample to form a specific shape.

S2.2. Place the flexible double-sided ultra-thin tape with higher viscosity (such as Silbione) on the surface of the PI substrate, place the cut sensor on the surface of the tape, and encapsulate it with a fiber film with lower viscosity to form a breathable fiber-made encapsulation layer, and then use a high-power (greater than 30 W) laser to cut the sample, to obtain a wireless sensor.

Example 4

A method for manufacturing a wireless sensor, including the following steps:

S1. Form a Sensing Element

Select a PI tape as the substrate, cut it to twice the size of the sensor, and use oxygen plasma to clean the surface of the PI substrate for two minutes. Coat a polyamic acid solution evenly on the surface of the PI substrate (50 L/cm$^2$). Due to the high viscosity of the polyamic acid solution, it needs to be left in the air for an hour to form a smooth surface. Place the sample on the heating stage, bake at 100° C. for one hour to remove the solvent, and then anneal at 150° C. for five minutes and 250° C. for one hour to obtain a thin film;

A $CO_2$ laser is used to induce molecular reconstruction of carbon-based groups on the surface of the film using a low-energy laser with a power of 6 to 20 W to form a resistance-sensitive layer.

A high-energy laser with a power of 20 to 35 W is used to modify, carbonize and cut the resistive sensitive layer to form a patterned sensing element.

The sensing element is patterned at a grating speed of 25%-75%, and linewidth resolution can be further improved through high-resolution lenses.

S2. Encapsulating to Prepare the Sensor

S2.1. Drop an insulating flexible encapsulation layer such as PDMS solution on the sensor surface to obtain a precursor sample. Place the precursor sample in a desiccator and vacuum it for five minutes to remove air bubbles. After leaving it overnight, the toluene solvent will evaporate. At this time, the sample is peeled off and attached to the surface of the PI substrate with its back side upward. The wire connection is covered with tape, and the insulating flexible encapsulation layer such as PDMS solution is spin-coated again to form a stretchable elastomer-made encapsulation layer. Then use a high-power (greater than 30 W) laser to cut the sample to form a specific shape.

S2.2. Place the flexible double-sided ultra-thin tape with higher viscosity (such as Silbione) on the surface of the PI substrate, place the cut sensor on the surface of the tape, and encapsulate it with a fiber film with lower viscosity to form a breathable fiber-made encapsulation layer, and then use a high-power (greater than 30 W) laser to cut the sample, to obtain a wireless sensor.

Example 5

A method for manufacturing a wireless sensor, including the following steps:

S1. Form a Sensing Element

Select a PI tape as the substrate, cut it to twice the size of the sensor, and use oxygen plasma to clean the surface of the PI substrate for two minutes. Coat a polyamic acid solution evenly on the surface of the PI substrate (50 L/cm$^2$). Due to the high viscosity of the polyamic acid solution, it needs to be left in the air for an hour to form a smooth surface. Place the sample on the heating stage, bake at 100° C. for one hour to remove the solvent, and then anneal at 150° C. for five minutes and 250° C. for one hour to obtain a thin film;

A $CO_2$ laser is used to induce molecular reconstruction of carbon-based groups on the surface of the film using a low-energy laser with a power of 6 to 20 W to form a resistance-sensitive layer.

A high-energy laser with a power of 20 to 35 W is used to modify, carbonize and cut the resistive sensitive layer to form a patterned sensing element.

The sensing element is patterned at a grating speed of 25%-75%, and linewidth resolution can be further improved through high-resolution lenses.

S2. Encapsulating to Prepare the Sensor

S2.1. Drop an insulating flexible encapsulation layer such as PDMS solution on the sensor surface to obtain a precursor sample. Place the precursor sample in a desiccator and vacuum it for five minutes to remove air bubbles. After leaving it overnight, the toluene solvent will evaporate. At this time, the sample is peeled off and attached to the surface of the PI substrate with its back side upward. The wire connection is covered with tape, and the insulating flexible encapsulation layer such as PDMS solution is spin-coated again to form a stretchable elastomer-made encapsulation layer. Then use a high-power (greater than 30 W) laser to cut the sample to form a specific shape;

S2.2. Place the flexible double-sided ultra-thin tape with high viscosity (such as Silbione) on the surface of the PI substrate. Place the cut sensor on the surface of the tape and encapsulate it with a non-adhesive fiber layer to form a breathable fiber-made encapsulation layer, and then use a high-power (greater than 30 W) laser to cut the sample to obtain a wireless sensor.

Figure 6:
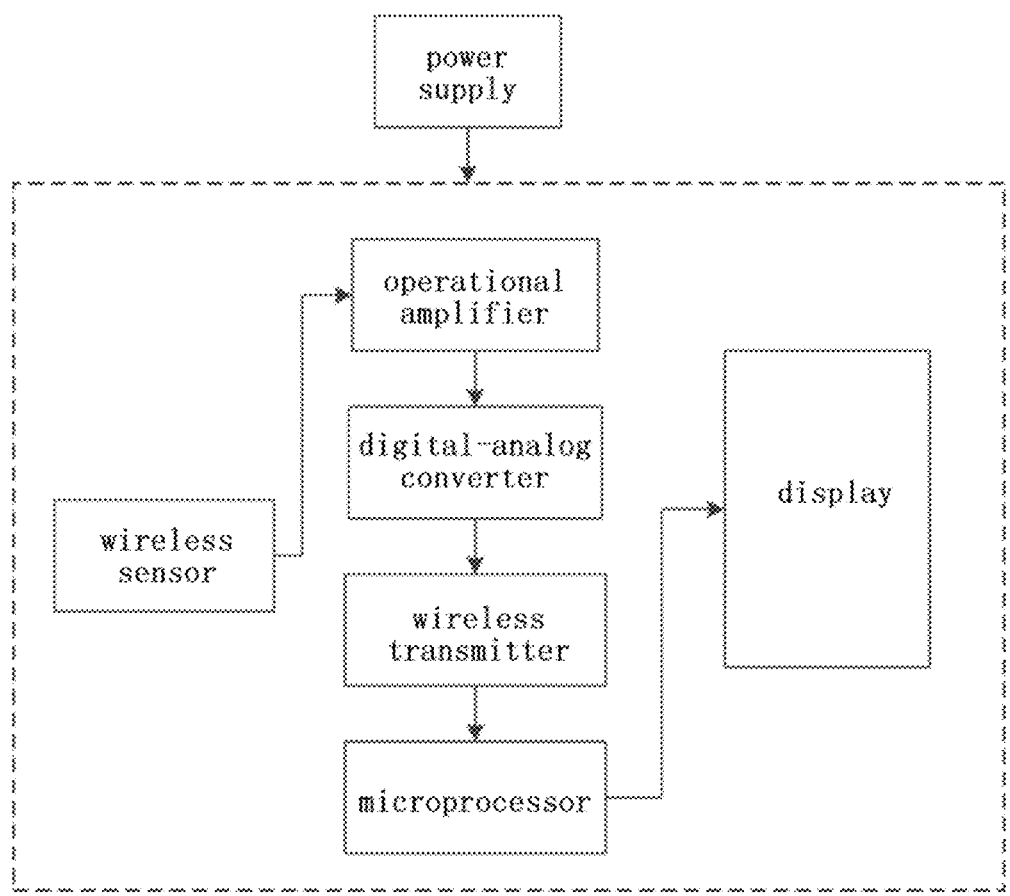
FIG. 6 is a schematic flow chart of a wound flatness detection system in one embodiment.
Figure 7:
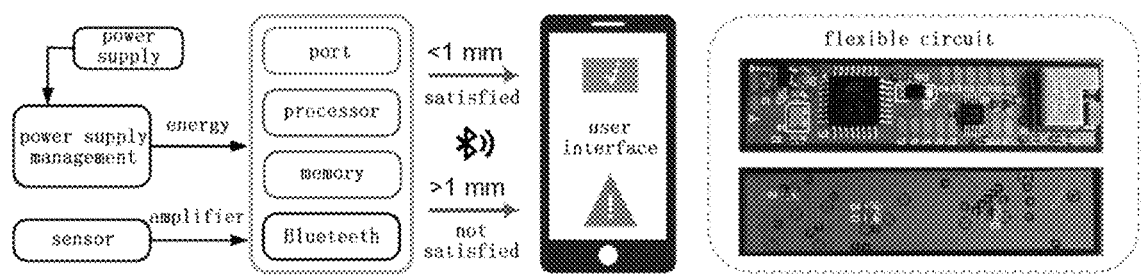
FIG. 7 is a framework flow chart and a power management schematic diagram of the wound flatness detection system in this embodiment.

FIG. 6 is a schematic flow chart of a wound flatness detection system in one embodiment. FIG. 7 is a framework flow chart and a power management schematic diagram of the wound flatness detection system in this embodiment. The curvature adaptation of the overall structure is achieved through flexible circuit board integration.

Next, a wound flatness detection system is prepared using the wireless sensor prepared in the above embodiment.

Example 6

Please refer to FIGS. 6 to 7 for a wound flatness detection system, including a power supply, a microprocessor, an operational amplifier, a digital-analog converter, a wireless transmitter, a display and a wireless sensor; the power supply is electrically connected to the microprocessor, the operational amplifier, the digital-analog converter, the wireless transmitter, the display, and the wireless sensor. The wireless sensor is the wireless sensor of Example 2.

The wireless sensor is disposed on the wound surface. The wireless sensor can sense the flatness of the wound and convert it into a resistance signal.

The operational amplifier is used to receive the resistance signal and convert it into a voltage signal.

The digital-analog converter is used to receive the voltage signal and convert it into a digital signal.

The wireless transmitter is used to receive the digital signal and wirelessly transmit it to the microprocessor. The wireless transmitter is a Bluetooth circuit module.

The microprocessor is used to receive the digital signal and send it to the display, and the user can observe the flatness of the wound surface through the digital signal displayed by the display.

The wireless sensor in the embodiment of the present disclosure can convert the postoperative wound flatness into changing resistance signals, and then the signals are read and transmitted through a wireless small circuit to monitor the wound suturing and healing conditions in real time on the user interface.

Figure 5:
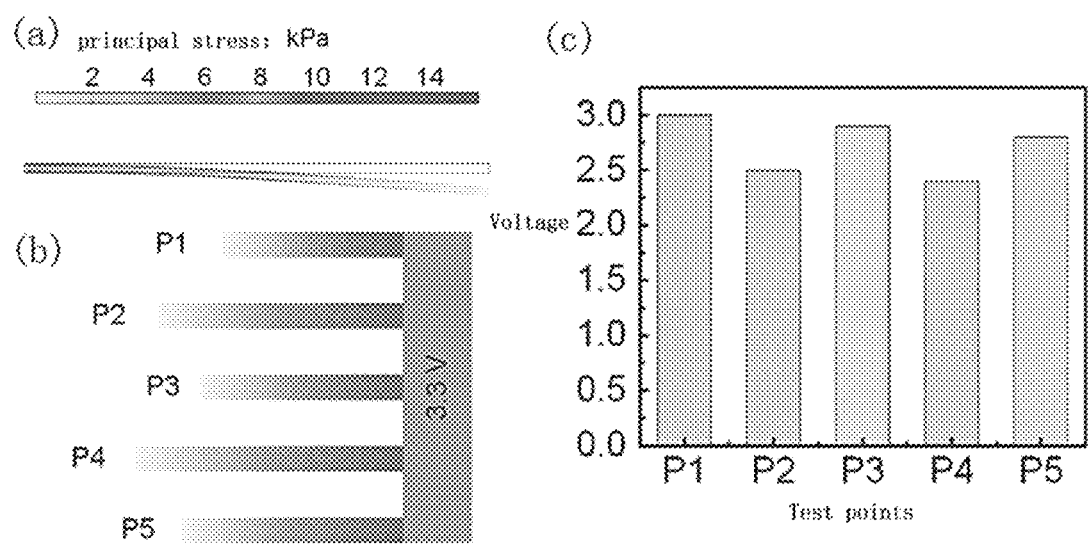
FIG. 5 shows the working principle and simulation diagram of the wireless sensor. (a) is a simulation diagram showing the uneven tensile stress of the electrode pins of the wireless sensor. (b) is a schematic diagram showing uneven stretching of 5 electrode pins of the wireless sensor. (c) is a voltage signal test chart corresponding to the uneven stretching of 5 electrode pins of the wireless sensor.

A simulation test was performed on the wound flatness detection system of Example 6, as shown in FIG. 5. FIG. 5 shows the working principle and simulation diagram of the wireless sensor. (a) is a schematic diagram showing the uneven tensile stress of the electrode pins of the wireless sensor. (b) is a schematic diagram showing uneven stretching of the five electrode pins of the wireless sensor. (c) is a voltage signal test chart corresponding to the uneven stretching of the five electrode pins of the wireless sensor.

As can be seen from FIGS. 2 and 5, the sensor in FIG. 2 has 5 electrode pins, corresponding to P1, P2, P3, P4, and P5 in FIG. 5(b). As shown in FIG. 5(a), the electrode pins of the wireless sensor in Example 2 can show uneven stretching on uneven wound surface. As a result, the five electrode pins of the wireless sensor form different degrees of stretching on the uneven wound surface, as shown in FIG. 5(b). Depending on the degree of stretching, different resistance distribution states are achieved, thus showing different partial voltages after the common potential port, resulting in differences in potential distribution at different test points, see FIG. 5(c). This shows that in the embodiment of the present disclosure, different resistance distribution states can be achieved through the different degrees of stretching formed by the multiple electrode pins of the sensor on the uneven surface, so that the partial voltages after the common potential port (3.3 V) are different, resulting in differences in potential distribution at different test points, which are used to determine the flatness of the wound.

According to the degree of stretch change of different electrode pins, for example, when the degree of stretch change is <1 mm, the flatness of the wound surface is satisfactory; when the degree of stretch change is >1 mm, the flatness of the wound surface is dissatisfied. The results of the change degree in the stretching of different electrode pins are displayed on the user interface, and the wound suturing and healing conditions are monitored in real time on the user interface, as shown in FIG. 7.

Example 7

There is provided a wound flatness detection system, including a power supply, a microprocessor, an operational amplifier, a digital-analog converter, a wireless transmitter, a display and a wireless sensor; the power supply is electrically connected to the microprocessor, the operational amplifier, the digital-analog converter, the wireless transmitter, the display, and the wireless sensor. The wireless sensor is the wireless sensor of Example 3.

The wireless sensor is disposed on the wound surface, and the wireless sensor can sense the flatness of the wound and convert it into a resistance signal.

The operational amplifier is used to receive the resistance signal and convert it into a voltage signal.

The digital-analog converter is used to receive the voltage signal and convert it into a digital signal.

The wireless transmitter is used to receive the digital signal and wirelessly transmit it to the microprocessor. The wireless transmitter is a Bluetooth circuit module.

The microprocessor is used to receive the digital signal and send it to the display, and the user can observe the flatness of the wound surface through the digital signal displayed by the display.

The wireless sensor of the present disclosure can convert the postoperative wound flatness into changing resistance signals, and then the signals are read and transmitted through a wireless small circuit to monitor the wound suturing and healing conditions in real time on the user interface.

A simulation test was performed on the wound flatness detection system of Example 7. The results showed that the five electrode pins of the sensor of Example 3 formed different stretching phenomena on the uneven wound surface. This proved that the electrode pins of the wireless sensor according to Example 3 form different degrees of stretching on the uneven wound surface. Depending on the degree of stretching, different resistance distribution states are achieved, thus showing different partial voltages behind the common potential port, resulting in different resistance distribution states at different test points. This shows that the embodiment of the present disclosure can achieve different resistance distribution states through the different stretching degrees of the multiple electrode pins of the sensor on the uneven surface, so that the partial voltages after the common potential port (3.3 V) are different, resulting in differences in potential distribution at different test points, which are used to determine the flatness of the wound.

According to the degree of stretch change of different electrode pins, for example, when the degree of stretch change is <1 mm, the flatness of the wound surface is satisfactory; when the degree of stretch change is >1 mm, the flatness of the wound surface is dissatisfied. The results of the change degree in the stretching of different electrode pins are displayed on the user interface, and the wound suturing and healing conditions are monitored in real time on the user interface.

Example 8

There is provided a wound flatness detection system, including a power supply, a microprocessor, an operational amplifier, a digital-analog converter, a wireless transmitter, a display and a wireless sensor; the power supply is electrically connected to the microprocessor, the operational amplifier, the digital-analog converter, the wireless transmitter, the display, and the wireless sensor. The wireless sensor is the wireless sensor of Example 4.

The wireless sensor is disposed on the wound surface, and the wireless sensor can sense the flatness of the wound and convert it into a resistance signal.

The operational amplifier is used to receive the resistance signal and convert it into a voltage signal.

The digital-analog converter is used to receive the voltage signal and convert it into a digital signal.

The wireless transmitter is used to receive the digital signal and wirelessly transmit it to the microprocessor. The wireless transmitter is a Bluetooth circuit module.

The microprocessor is used to receive the digital signal and send it to the display, and the user can observe the flatness of the wound surface through the digital signal displayed by the display.

The wireless sensor of the present disclosure can convert the postoperative wound flatness into changing resistance signals, and then the signals are read and transmitted through a wireless small circuit to monitor the wound suturing and healing conditions in real time on the user interface.

A simulation test was performed on the wound flatness detection system of Example 8. The results showed that the five electrode pins of the sensor of Example 4 formed different stretching phenomena on the uneven wound surface. This proved that the electrode pins of the wireless sensor according to Example 4 form different degrees of stretching on the uneven wound surface. Depending on the degree of stretching, different resistance distribution states are achieved, thus showing different partial voltages behind the common potential port, resulting in different resistance distribution states at different test points. This shows that the embodiment of the present disclosure can achieve different resistance distribution states through the different stretching degrees of the multiple electrode pins of the sensor on the uneven surface, so that the partial voltages after the common potential port (3.3 V) are different, resulting in differences in potential distribution at different test points, which are used to determine the flatness of the wound.

According to the degree of stretching change of different electrode pins, for example, when the degree of stretching change is <1 mm, it indicates that the flatness of the wound surface is satisfactory; when the degree of stretching change is >1 mm, it indicates that the flatness of the wound surface is not satisfactory. The results of the changes in the stretching of different electrode pins are displayed on the user interface, and the wound suturing and healing conditions are monitored in real time on the user interface.

Example 9

There is provided a wound flatness detection system, including a power supply, a microprocessor, an operational amplifier, a digital-analog converter, a wireless transmitter, a display and a wireless sensor; the power supply is electrically connected to the microprocessor, the operational amplifier, the digital-analog converter, the wireless transmitter, the display, and the wireless sensor. The wireless sensor is the wireless sensor of Example 5.

The wireless sensor is disposed on the wound surface, and the wireless sensor can sense the flatness of the wound and convert it into a resistance signal.

The operational amplifier is used to receive the resistance signal and convert it into a voltage signal.

The digital-analog converter is used to receive the voltage signal and convert it into a digital signal.

The wireless transmitter is used to receive the digital signal and wirelessly transmit it to the microprocessor. The wireless transmitter is a Bluetooth circuit module.

The microprocessor is used to receive the digital signal and send it to the display, and the user can observe the flatness of the wound surface through the digital signal displayed by the display.

The wireless sensor of the present disclosure can convert the postoperative wound flatness into changing resistance signals, and then the signals are read and transmitted through a wireless small circuit to monitor the wound suturing and healing conditions in real time on the user interface.

A simulation test was performed on the wound flatness detection system of Example 9. The results showed that the five electrode pins of the sensor of Example 5 formed different stretching phenomena on the uneven wound surface. This proved that the electrode pins of the wireless sensor according to Example 5 form different degrees of stretching on the uneven wound surface. Depending on the degree of stretching, different resistance distribution states are achieved, thus showing different partial voltages behind the common potential port, resulting in different resistance distribution states at different test points. This shows that the embodiment of the present disclosure can achieve different resistance distribution states through the different stretching degrees of the multiple electrode pins of the sensor on the uneven surface, so that the partial voltages after the common potential port (3.3 V) are different, resulting in differences in potential distribution at different test points, which are used to determine the flatness of the wound.

According to the degree of stretching change of different electrode pins, for example, when the degree of stretching change is <1 mm, it indicates that the flatness of the wound surface is satisfactory; when the degree of stretching change is >1 mm, it indicates that the flatness of the wound surface is not satisfactory. The results of the changes in the stretching of different electrode pins are displayed on the user interface, and the wound suturing and healing conditions are monitored in real time on the user interface.

Example 10

There is provided a wound flatness detection system, including a power supply, a microprocessor, an operational amplifier, a digital-analog converter, a wireless transmitter, a display and a wireless sensor; the power supply is electrically connected to the microprocessor, the operational amplifier, the digital-analog converter, the wireless transmitter, the display, and the wireless sensor. The wireless sensor is the wireless sensor of Example 2.

The wireless sensor is disposed on the wound surface, and the wireless sensor can sense the flatness of the wound and convert it into a resistance signal.

The operational amplifier is used to receive the resistance signal and convert it into a voltage signal.

The digital-analog converter is used to receive the voltage signal and convert it into a digital signal, and the user can observe the flatness of the wound surface through the digital signal displayed by the display.

The wireless transmitter is used to receive the digital signal and wirelessly transmit it to the microprocessor. The wireless transmitter is an NFC module.

The microprocessor is used to receive the digital signal and send it to the display.

The wireless sensor of the present disclosure can convert the postoperative wound flatness into changing resistance signals, and then the signals are read and transmitted through a wireless small circuit to monitor the wound suturing and healing conditions in real time on the user interface.

A simulation test was performed on the wound flatness detection system of Example 10. The results showed that the five electrode pins of the sensor of Example 2 formed different stretching phenomena on the uneven wound surface. This proved that the electrode pins of the wireless sensor according to Example 2 form different degrees of stretching on the uneven wound surface. Depending on the degree of stretching, different resistance distribution states are achieved, thus showing different partial voltages behind the common potential port, resulting in different resistance distribution states at different test points. This shows that the embodiment of the present disclosure can achieve different resistance distribution states through the different stretching degrees of the multiple electrode pins of the sensor on the uneven surface, so that the partial voltages after the common potential port (3.3 V) are different, resulting in differences in potential distribution at different test points, which are used to determine the flatness of the wound.

According to the degree of stretching change of different electrode pins, for example, when the degree of stretching change is <1 mm, it indicates that the flatness of the wound surface is satisfactory; when the degree of stretching change is >1 mm, it indicates that the flatness of the wound surface is not satisfactory. The results of the changes in the stretching of different electrode pins are displayed on the user interface, and the wound suturing and healing conditions are monitored in real time on the user interface.

In summary, the above-mentioned examples/embodiments of the present disclosure use a carbon-based polymer solution to prepare a thin film, and then uses laser as an energy source to achieve patterning of the sensing element through two-step laser induction, which is beneficial to converting the flatness of the wound into a resistance signal and improving detection sensitivity. The sensing element is encapsulated in the upper and lower layers and composited with a fiber layer, which enables the wireless sensor to have high multi-layer matching degree and the ability to resist environmental interference. It can also avoid static interference from the human body and ensure that the mechanical relationship between the sensing layer and the substrate is satisfied, and it is capable of achieving a breathable and viscosity-controllable design. The prepared wireless sensor is used to convert the postoperative wound flatness into changing resistance signals, and the signals are read and transmitted through a wireless small circuit to monitor the wound suturing and healing conditions in real time on the user interface, to realize the detection and recovery observation of postoperative wounds. It has important application value.

The above are only optional embodiments of the present disclosure but are not intended to limit the present disclosure. Any modifications, equivalent substitutions and improvements made within the spirit and principle of the present disclosure shall fall within the protection scope of the present disclosure.

What is claimed is:

1. A wireless sensor configured for sensing a flatness of a wound surface and convert the flatness into a resistance signal, comprising a sensing element (2), two elastomer-made encapsulation layers (1) and a breathable fiber-made encapsulation layer (3), wherein the sensing element (2) is arranged between the two elastomer-made encapsulation layers (1), and the breathable fiber-made encapsulation layer (3) is disposed on one of the elastomer-made encapsulation layers (1);

wherein the sensing element (2) is manufactured by the following steps:

step 1: preparing a thin film using a carbon-based polymer solution;

step 2: using a low-energy laser to induce molecular reconstruction of carbon-based groups on surfaces of the thin film to form a resistance-sensitive layer; in step 2, the low-energy laser has a power of 6-20 W;

step 3: using a high-energy laser to modify, carbonize and cut the resistance-sensitive layer to form a patterned sensing element; in step 3, the high-energy laser has a power of 20-35 W, wherein the sensing element (2) has a plurality of electrode pins (21) at one side; the plurality of electrode pins have different degrees of stretching on an uneven surface, achieving different resistance distribution states;

wherein the elastomer-made encapsulation layers (1) comprise SEBS layers, and the SEBS layers are formed by coating and solidifying a SEBS solution on surfaces of the sensing element (2).

2. The wireless sensor according to claim 1, wherein in step 1, the preparing a thin film using a carbon-based polymer solution comprises:

evenly coating the carbon-based polymer solution on a surface of a substrate, drying the surface of the substrate to remove solvent, and then performing an annealing treatment to the substrate to obtain the thin film.

3. The wireless sensor according to claim 2, wherein the carbon-based polymer solution is a polyamic acid solution; the substrate is a polyimide substrate or a glass substrate;

the annealing treatment is performed in such a condition that an annealing temperature is 150-250° C. and an annealing time is 5-60 minutes.

4. The wireless sensor according to claim 1, wherein the breathable fiber-made encapsulation layer (3) comprises an adhesive layer and a fiber film, and the fiber film is connected to the elastomer-made encapsulation layer (1) through the adhesive layer.

5. The wireless sensor according to claim 1, wherein the sensing element (2), the elastomer-made encapsulation layer (1) and the breathable fiber-made encapsulation layer (3) have the same shape; the sensing element (2), the elastomer-made encapsulation layer (1) and the breathable fiber-made encapsulation layer (3) have the same dimension.

6. A method for manufacturing the wireless sensor according to claim 4, comprising the following steps:

S1: preparing a thin film using a carbon-based polymer solution;

S2: using a low-energy laser to induce molecular reconstruction of carbon-based groups on surfaces of the thin film to form a resistance-sensitive layer;

S3: using a high-energy laser to modify, carbonize and cut the resistance-sensitive layer to form a patterned sensing element (2);

S4: coating and solidifying a SEBS solution on one surface of the sensing element (2) to form a SEBS layer; after peeling and flipping, coating and solidifying a SEBS solution on the other surface of the sensing element (2) to form another SEBS layer; using a high-energy laser to carbonize and cut two SEBS layers to form patterned elastomer-made encapsulation layers (1);

S5: encapsulating a fiber film on one of the elastomer-made encapsulation layers (1) through adhesive; using a high-energy laser to carbonize and cut the fiber film to form a patterned breathable fiber-made encapsulation layer (3).

7. The method for manufacturing the wireless sensor according to claim 6, wherein in step S1, the preparing a thin film using a carbon-based polymer solution comprises: evenly coating the carbon-based polymer solution on a surface of a substrate, drying the surface of the substrate to remove solvent, and then performing an annealing treatment to the substrate to obtain the thin film;

the carbon-based polymer solution is a polyamic acid solution; the substrate is a polyimide substrate or a glass substrate; the annealing treatment is performed in such a condition that an annealing temperature is 150-250° C. and an annealing time is 5-60 minutes.

8. A wound flatness detection system, comprising a microprocessor, an operational amplifier, a digital-analog converter, a wireless transmitter, a display and the wireless sensor according to claim 1;
   the wireless sensor is configured to sense a flatness of a wound surface and convert it into a resistance signal;
   the operational amplifier is configured to receive the resistance signal and convert it into a voltage signal;
   the digital-analog converter is configured to receive the voltage signal and convert it into a digital signal;
   the wireless transmitter is configured to receive the digital signal and wirelessly transmit it to the microprocessor;
   the microprocessor is configured to receive the digital signal and send it to the display.

\* \* \* \* \*